(12) United States Patent
Haddad et al.

(10) Patent No.: US 12,722,994 B2
(45) Date of Patent: Sep. 1, 2026

(54) REDUCED-HEADSPACE DIGESTER

(71) Applicants: SUEZ INTERNATIONAL, Paris la Defense Cedex (FR); XL BETEILIGUNGEN GMBH & CO. KG, Tannhausen (DE)

(72) Inventors: Mathieu Haddad, Sevres (FR); Valéry Geaugey, Paris la Defense Cedex (FR); Cynthia Berlou, Paris la Defense Cedex (FR); Manuel Lipp, Ellwangen (DE); Pedro Benard Guedes Lopes Da Fonseca, São Domingos de Rana (PT)

(73) Assignees: SUEZ INTERNATIONAL, Paris la Defense Cedex (FR); XL BETEILIGUNGEN GMBH & CO. KG, Tannhausen (DE)

( * ) Notice: Subject to any disclaimer, the term of this patent is extended or adjusted under 35 U.S.C. 154(b) by 409 days.

(21) Appl. No.: 18/549,066

(22) PCT Filed: Mar. 7, 2022

(86) PCT No.: PCT/EP2022/055673
§ 371 (c)(1),
(2) Date: Sep. 5, 2023

(87) PCT Pub. No.: WO2022/189324
PCT Pub. Date: Sep. 15, 2022

(65) Prior Publication Data

US 2024/0166544 A1 May 23, 2024

(30) Foreign Application Priority Data

Mar. 8, 2021 (FR) ...................................... 2102210

(51) Int. Cl.
*C02F 11/04* (2006.01)
*C02F 3/08* (2023.01)
(Continued)

(52) U.S. Cl.
CPC ................ *C02F 11/04* (2013.01); *C02F 3/08* (2013.01); *C02F 3/2866* (2013.01); *C12M 1/107* (2013.01);
(Continued)

(58) Field of Classification Search
CPC ......... C02F 11/04; C02F 3/08; C02F 3/2866; C02F 2301/046; C12M 1/107;
(Continued)

(56) References Cited

U.S. PATENT DOCUMENTS 1,806,698 A * 5/1931 Miller ...................... C02F 3/28 210/194
4,530,762 A * 7/1985 Love ...................... C12M 21/04 210/603
(Continued)

FOREIGN PATENT DOCUMENTS

CN 112794596 A * 5/2021 .............. C02F 11/04
EP 1993693 A2 11/2008
(Continued)

OTHER PUBLICATIONS

Machine-generated English translation of FR 3007023, generated on Nov. 10, 2025.*
(Continued)

*Primary Examiner* — Fred Prince
(74) *Attorney, Agent, or Firm* — LEASON ELLIS LLP

(57) ABSTRACT

The invention concerns a digester for performing a sludge methanization treatment for the purpose of generating biogas and a digestate, the digester comprising a device (32) for discharging foaming and/or floating matter (16) from the digestate (12), comprising: a first tank (33) delimited by a first wall (100) having a first height (h1), the first tank (33) being intended to be fed with digestate (12) and with
(Continued)

Figures 1, 2:
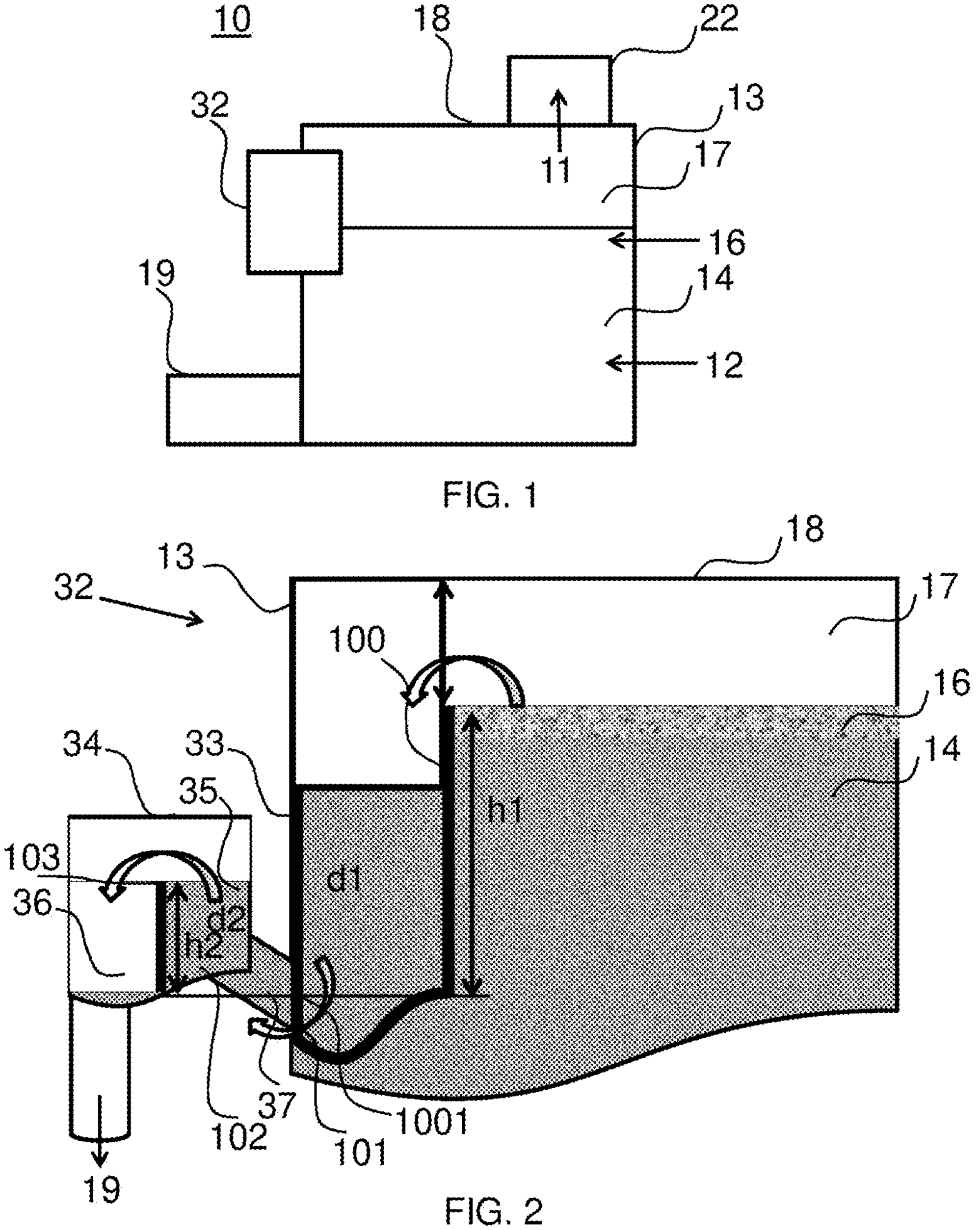

foaming and/or floating matter (16) from a volume of material (14) by overflow over the first wall (100); a second tank (34) connected to the atmosphere and sited outside the enclosure (13) of the digester, comprising: a first zone (35) delimited by a second wall (103) having a second height (h2); and a second zone (36) in communication with the reservoir (19); a conduit (37) connecting the first tank (33) via a first orifice (101) to the first zone (35) of the second tank (34) via a second orifice (102) positioned higher than or level with the first orifice (101), the first zone (35) being intended to be fed with digestate (12) and with foaming and/or floating matter (16) from the first tank (33) through the conduit (37); the second zone (36) being intended to be fed with digestate from the first zone (35) by overflow over the second wall (103); the first height (h1) and the second height (h2) being predefined such that a first mixture, containing variable proportions of digestate and foaming and/or floating matter in the first tank (33) and having a first average density (d1), is transferred by gravity into the first zone (35), which contains a second mixture containing variable proportions of digestate and foaming and/or floating matter and having a second density (d2), the transfer operating such that the product of the first average density (d1) times the first height (h1) is greater than the product of the second average density (d2) times the second height (h2) times the first height (h1).

11 Claims, 6 Drawing Sheets

(51) Int. Cl.

| | |
|---|---|
| ***C02F 3/28*** | (2023.01) |
| ***C12M 1/00*** | (2006.01) |
| ***C12M 1/10*** | (2006.01) |
| ***C12M 1/107*** | (2006.01) |
| ***C12M 1/21*** | (2006.01) |
| ***C12M 1/34*** | (2006.01) |

(52) U.S. Cl.
CPC ............ *C12M 21/04* (2013.01); *C12M 29/18* (2013.01); *C12M 41/02* (2013.01); *C12M 41/44* (2013.01); *C12M 47/18* (2013.01); *C02F 2301/046* (2013.01); *Y02E 50/30* (2013.01)

(58) Field of Classification Search
CPC ...... C12M 21/04; C12M 29/18; C12M 41/02; C12M 41/44; C12M 47/18; Y02E 50/30
USPC .................................................. 210/603, 194
See application file for complete search history.

(56) References Cited

U.S. PATENT DOCUMENTS 4,551,243 A * 11/1985 Martin .................. C12M 41/24 71/10
6,942,801 B2 * 9/2005 Nishimura ............. C02F 11/02 210/194
7,708,885 B2 * 5/2010 Lanting .................. C12M 27/20 210/603
2012/0252066 A1 10/2012 Heng
2020/0156963 A1 * 5/2020 Bronk ..................... C02F 1/004

FOREIGN PATENT DOCUMENTS

FR 3007023 A1 * 12/2014 ................ C02F 3/28
KR 100485639 B1 * 4/2005 .............. C02F 11/04

OTHER PUBLICATIONS

Machine-generated English translation of CN 112794596, generated on Nov. 10, 2025.*

Machine-generated English translation of KR 100485639, generated on Nov. 10, 2025.*

"Schnaars Kenneth et al. ""The Trials and Tribulations of Commissioning a Large Biosolids Facility; An Operational Perspective"" Proceedings of the Water Environment Federation, Jan. 1, 2017 (Jan. 1, 2017), Retrieved from the Internet:https://www.mi-wea.org/docs/8B-Schnaars_Ken-Michigan_BiosolidsConference.pdf [retrieved on Oct. 29, 2021] DOI: 10.2175/193864717821496293 XP055856284 p. 34-p. 35".

Wilson Tom. "Digester Foaming Problems and Solutions" Mar. 15, 2013 (Mar. 15, 2013). Retrieved from the Internet: http://cswea.org/wp-contenUuploads/2017/09/DigersterFoamingSolutions.pdf [retrieved on Oct. 29, 2021] XP055856292 p. 40 p. 44-p. 45.

International Search Report and Written Opinion in PCT Application No. PCT/EP2022/055673, mailed May 25, 2022, an English translation attached hereto (12 pages).

* cited by examiner

REDUCED-HEADSPACE DIGESTER

CROSS-REFERENCE TO RELATED PATENT APPLICATIONS

This application is a U.S. National Stage Application under 35 U.S.C. § 371 of International Patent Application No. PCT/EP2022/055673 filed Mar. 7, 2022, which claims the benefit of priority of French Patent Application No. 2102210 filed Mar. 8, 2021, both of which are incorporated by reference in their entireties. The International Application was published on Sep. 15, 2022, as International Publication No. WO/2022/189324 A1.

The invention lies in the technical field of the biological treatment of sludge, in particular derived from wastewater. The invention relates to a digester for performing a sludge methanization treatment.

Methanization is a technology based on the degradation of organic matter by microorganisms, under controlled conditions and in the absence of oxygen, and therefore in an anaerobic environment. It is also referred to as anaerobic digestion.

Methanization makes it possible to generate:

- a digestate, which is a wet product, rich in partially stabilized organic matter. It is generally planned to return the digestate back to the ground, optionally after a composting maturation phase;
- biogas, a gas mixture generally saturated with water at the outlet of the digester and typically composed of about 50% to 70% methane (CH4), 30% to 50% carbon dioxide (CO2) and some trace gas ($NH_3$, $N_2$, $H_2S$). Biogas constitutes renewable energy, and it may be injected into the natural gas network after purification. Biogas can also be used for the production of electricity and heat and/or the production of a fuel.

One of the advantages of methanization is the recovery of organic matter and the production of energy via the biogas generated.

Methanization is carried out in a digester. The digester can be seen as an enclosure closed by an upper wall (also called a roof), defining two volumes: a first volume containing the material to be treated, the sludge, the generated digestate, and a second volume between the first volume and the upper wall, also called the headspace, and toward which the generated biogas rises.

The term "sludge" should be understood as being any organic matter, including organic waste and all kinds of sludges, including primary sludges, biological sludges, activated sludges, and more particularly sludges of organic waste or purification plants for drinking water or wastewater. Organic matter, or natural organic matter, refers to the large source of carbon-based compounds that are found in natural and artificial, land and aquatic environments. It is matter composed of organic compounds coming from the remains of organisms such as plants and living beings and their waste in the environment. Organic molecules can also be manufactured by chemical reactions that do not involve life. The basic structures are created from cellulose, tannin, cutin and lignin, as well as other proteins, lipids and carbohydrates.

Safety problems may be related to the implementation of a digester. Indeed, biogas contains methane, which creates a risk of explosion inside the digester if oxygen accidentally penetrates the digester. As a result, stand-off distances due to the presence of biogas in the digester are defined in order to delimit a so-called risk perimeter.

Blast overpressure is the consequence of an explosion which manifests itself by the propagation, from the zone of the explosion, of a pressure wave in the atmosphere, at a speed of approximately that of sound waves (340 m/s in air at 15° C.). When the characteristics of such a wave are measured at a fixed point of space, a positive pressure pulse (overpressure)—the duration of which is generally measured in milliseconds—is observed, followed by a negative pressure phase.

If the explosion originates from the detonation of an explosive substance, the positive overpressure is characterized by a very sudden rise, virtually instantaneous, to the maximum pressure, followed by a quasi-linear decrease. The negative pressure peak is much less significant and it is generally not considered when evaluating the effects of a pressure wave.

The pressure is a force per unit of area likely to induce bending or shear forces in the structures, optionally compression structures for the human body. A pressure wave can also propel projectiles.

In France, the order of Oct. 22, 2004 (Ministry of Ecology and Sustainable Development) defines the standard threshold values of effects of accidental phenomena of classified facilities. These values are used to determine zones of potential accident effects in hazard studies (blast radii).

When the breaking pressure of a digester is known, the calculation of the explosion energy can be carried out with the so-called Brode equation. This energy is the energy that can be used in missile propulsion or the production of overpressure waves or heat fluxes, according to:

$$E = \frac{\Delta P \cdot V}{\gamma r - 1}$$

Where ΔP is: Pr−P0; Pr: Breaking pressure of the enclosure (Pa); P0: Atmospheric pressure (Pa); V: Volume of headspace (m3); γr: Ratio of the specific heats of the gas contained in the tank (1,4 for methane); E: Explosion energy (J).

Once the explosion energy has been determined, there are several methods for calculating stand-off distances. In the case of a digester, the Multi-Energy TNO model is mainly used, for confined or unconfined explosions (Unconfined Vapor Cloud Explosion (UVCE)).

The problem therefore lies in reducing stand-off distances caused by the presence of biogas. Looking at digesters conceptually, the two adjustable parameters that impact the level of the overpressure thresholds and the stand-off distances of the explosion are:

- The breaking pressure of the structure;
- The explosive volume (that is, the volume of the headspace during normal operation or of the empty digester during accidental emptying).

The headspace is generally quite large, and the distance between the level of digestate and the upper wall of the digester can be up to 3 m. Such a height is first of all intended to allow the accumulation of floating products and to manage any foam caused either by the presence of filamentous bacteria in the method for decontaminating wastewater producing sludge (sludge overrun, called "bulking"), or by the production of surfactant compounds in the digester. Indeed, most often, digesters do not have a device for discharging foams and floating products. It is therefore necessary to provide such a "storage" volume on the surface of the digestate.

Furthermore, the tallness of the headspace also makes it possible to manage a possible phenomenon of rapid expansion of the volume of digestate (known as RVE for "Rapid Volume Expansion"). RVE is a phenomenon linked to the sudden increase in viscosity of the digestate, caused, most often, by a loss or a disruption of the mixing function. Indeed, once the shearing decreases, the viscosity of the digestate increases, which traps some of the biogas in the digestate, and can generate a rapid increase in the volume thereof.

In summary, the usual design of digesters consists of leaving a great height between the level of digestate and the upper wall of the digester, so as to be able to store the foams and floating products on the surface of the digestate and to allow a possible phenomenon of RVE. If this height is insufficient, the integrity of the structure—more particularly that of the upper wall—is endangered. This available volume for the expansion of the foams is usually occupied by biogas, and leads to the safety constraints mentioned above.

It is therefore interesting to reduce the volume of biogas in the upper part of the digester to reduce the stand-off distances in the event of an explosion. Reducing this volume of biogas without taking risks with the integrity of the digester, however, requires the continuous removal (1) of foams and floating products from the surface of the digestate, and (2) the volume of digestate that can be contained in the digester in the case of an RVE phenomenon without exerting overpressure.

However, the extraction of foams and floating matter on the surface is a complex operation to perform. A first solution to this problem consists of extracting the digestate therefrom by simple overflow. This makes it possible to periodically drive out "packets" of foaming/floating matter present on the surface. Nevertheless, with such a solution, the gas contained on the surface of the digester can escape via the overflow device. To avoid this, another downstream device must be provided to retain the biogas and separately collect the digestate containing the foaming/floating matter. These devices generally operate on the principle of the hydraulic seal, the operation of which is mainly dictated by the density of the treated liquid. However, the density of the digestate containing the foaming/floating matter varies greatly over time: When the packets of foaming/floating matter are extracted, the density drops sharply, which prevents the proper operation of the hydraulic seal. Another difficulty lies in the fact that these devices downstream of the overflow must meet two opposing constraints: Have a hydraulic cross-section that is small enough to produce high speeds that make it possible to drive out the foaming/floating matter, and have sufficiently wide hydraulic sections to prevent clogging by the digestate and the foaming/floating matter. This first solution, using a simple overflow, is therefore not completely satisfactory.

Second solution consists of extracting the digestate from the foams and floating matter via a buried orifice close to the surface. The extraction in this case is generally "passive". This makes it possible to simply contain the biogas in the digester, but poses safety problems in the event of an uncontrolled decrease in the liquid level. Indeed, in this case, biogas can escape. Furthermore, this solution actually has a low efficiency at driving out the foaming/floating matter.

Another solution may consist of managing the consequences of foaming without seeking to evacuate the foaming/floating matter. Thus, when foaming takes place and is detected, digestate is extracted—for example by "active" pumping -so as to partially empty the digester in order to prevent the foam from pressuring the roof of the digester. The pumped digestate is poured into an exterior reservoir provided for this purpose. Although such a device meets safety requirements by artificially increasing the height of the headspace, it has the disadvantage of at least partially emptying the contents of the digester. The reaction volume is then reduced, with negative impacts on the performance of the digester. If it is possible to expect a return "to normal" in the event of reversible foaming, this solution does not make it possible to wait for a return to normal in the event of accumulation of floating matter with recurring or permanent foaming. In the latter cases, a "long-lasting" operation of the digester is then achieved with an augmented gas phase volume that is detrimental to the security objective with respect to explosion risks, associated with a reduction in the effective volume of the digester, therefore its treatment capacity.

WO 2009/118320 for its part proposes a digester aiming to reduce the effect of the explosion by minimizing the explosive volume using a space provided to allow the biogas to escape from the sludge without generating light foam of the surfactant type, while allowing the accumulation of a certain volume of floating matter (distinct from light foam) and while managing RVE. In this approach, the digester comprises an inverted bell that recovers the biogas produced and a device allowing access to the mixer to be able to take it out without requiring the digester to be drained. Furthermore, the injection of water (industrial) is implemented to break up any foams formed in the digester and to cool the biogas. However, this digester has several drawbacks. First, in the event that the supply of water stops, the foam can no longer be contained by the digester. The foam may then invade the biogas network, with risks of non-operation of the flare and high-pressure losses in the networks, leading to exceeding the breaking pressure in the digester. Second, although the injection of water described in WO 2009/118320 makes it possible to break up light foams (like white foams of surfactants), it is not effective against thick and oily foams caused by filamentous biological sludge and/or floating materials coated with fats and grooves with biogas, with similar consequences to those encountered in the case of stopping the supply of water. In particular, in the event of overflow of the digester, very rapid clogging of the biogas network is observed, as well as any additional safety valves, which results in a first stage in causing sludge to exit through the feed basin, then, in a second step, a direct exiting of the biogas produced through that same basin.

Discharging the foaming/floating matter is envisaged, but it is provided to go to a tank placed outside the digester. The gas phase of this external tank communicates with the headspace of the digester, so it is not easy to extract the floating foams from this external tank without simultaneously causing a biogas leak, generating risks of explosion outside the digester, with the disadvantages and risks mentioned above.

U.S. Pat. No. 4,530,762 describes a digester comprising a device for discharging the foaming/floating matter of the digestate. Any content going to the first tank in the enclosure of this digester appears to be transferred to the first zone of the tank. The tanks are intended to recover the treated effluent and are arranged on a bed of tubular decanters. The second tank is a gas separator. In normal operation, a wall must be positioned with its upper end in horizontal alignment with the edges of the tanks. Raising the wall allows the foams to be driven into the tanks. The foams are then collected in the tank and blown out of the tank when necessary. In other words, to consider the discharge of the foams, the wall must be in the high position relative to the nominal position, and therefore at a higher altitude than the edges of the tanks. Furthermore, in this digester, it is impossible to collect the foams with a first submerged tank.

Finally, U.S. Pat. No. 5,228,995 describes a reduced-headspace digester with an enclosure composed of three zones:

- the first lower zone contains the digestate,
- the second middle zone consists of a structural steel support for accommodating a filter medium forming a surface to which a biological deposit may attach. This zone is a solid/liquid/gas separation zone,
- The third upper zone contains the clarified liquid fraction. The treated effluent is extracted from this zone by a submerged pipework system and a system for controlling the treated effluent.

Thus, this digester requires an additional foam-breaking system to operate correctly.

There is therefore a need for a reduced-headspace digester that is simple to implement, making it possible both to maintain the integrity of the structure in the event of an RVE phenomenon and to discharge the foams regardless of their density, i.e., capable of discharging not just low-density foams but also thick fatty foams.

The invention aims to overcome all or some of the problems cited above by proposing a reduced-headspace digester comprising a gravity-operated foam discharge device and a double overflow device. In one embodiment, the digester comprises a digestate mixing device coupled to a device for injecting digestate into the headspace, serving both to direct the foams and floating matter on the surface toward the first overflow and to break up the foams by mechanical effect. Such a digester makes it possible to reconcile operational safety and digester headspace volume reduction, which thus reduces the level of the overpressure thresholds and the stand-off distances by working on the two adjustable parameters that are the breaking pressure of the structure and the explosive volume (volume of the headspace).

To this end, the invention relates to a digester intended to perform a sludge methanization treatment for generating biogas and a digestate, the digester comprising:

- an enclosure intended to contain a volume of material, the volume of material comprising the digestate, the digestate comprising at its surface foams and/or floating matter coming from the sludge or generated during the methanization treatment, the enclosure defining a first volume equal to the volume of material and a second volume disposed above the first volume;
- a roof intended to close the enclosure;
- a reservoir near the enclosure and intended to collect the digestate,
- a dome arranged on a portion of the roof and intended to collect the biogas, the digester being characterized in that it comprises a device for discharging the foams and/or floating matter of the digestate comprising:
- a first tank arranged in the enclosure and delimited by a first wall, the first tank being intended to be fed with digestate and foam and/or floating matter from the volume of material by overflow above the first wall;
- a second tank connected to the atmosphere and sited outside the enclosure, comprising:
  - a first zone delimited by a second wall; and
  - a second zone in communication with the reservoir;
- a conduit connecting the first tank via a first orifice to the first zone of the second tank via a second orifice,
- the first zone being intended to be fed with digestate and with foaming and/or floating matter from the first tank through the conduit; the second zone of the second tank being intended to be fed with digestate from the first zone of the second tank by overflow over the second wall; the second orifice being positioned higher than or level with the first orifice;

the upper end of the first wall being located at a first height above a reference point of the first orifice and the upper end of the second wall being located at a second height above the reference point of the first orifice;

the first height and the second height being predefined such that a first mixture, containing variable proportions of digestate and foaming and/or floating matter in the first tank and having a first average density, is transferred by gravity into the first zone, which contains a second mixture containing variable proportions of digestate and foaming and/or floating matter and having a second density, the transfer operating such that the product of the first average density times the first height is greater than the product of the second average density times the second height times the first height.

In one embodiment, the digester according to the invention further comprises a device for mixing the volume of material disposed in the first volume, the mixing device being configured to move the volume of material.

Advantageously, the mixing device comprises:

- One or more chimneys extending into the enclosure along a first axis, preferably at the periphery of the enclosure, each chimney having an upper end and a lower end;
- One or more first mixers, each preferably positioned under the lower end of one of the chimneys, the first mixer(s) being configured to move the volume of material in rotation around a vertical central axis, substantially parallel to the first axis and in translation along the first axis from the upper end toward the lower end of said chimney.

Advantageously, the mixing device comprises one or more second mixers, each being arranged in the enclosure, preferably in the bottom of the enclosure, and more preferably at the periphery of the enclosure, the second mixers being configured to move the volume of material in rotation around a vertical central axis, substantially parallel to the first axis.

In another embodiment, the digester according to the invention further comprises a device for injecting digestate into the second volume, preferably arranged at the center of the roof, and/or in the volume of material.

Advantageously, the digestate injection device comprises:

- A first injector attached to the roof, preferably to the center of the roof, and in fluid connection with the second volume and configured to inject digestate into the second volume;
- A first recirculation loop between the first volume and the first injector;
- A first recirculation pump configured to recirculate the digestate in the first recirculation loop from the first volume to the first injector.

Advantageously, the digestate injection device further comprises:

- A second injector attached to a side wall of the enclosure at a first height and in fluid connection with the enclosure and configured to inject digestate into the enclosure at the first height;
- A second recirculation loop between a second height of the enclosure, which is less than the first height, and the second injector;

A second recirculation pump configured to recirculate the digestate in the second recirculation loop from the second height of the enclosure and to the second injector.

In another embodiment, the first recirculation loop and the second recirculation loop are grouped into one and the same recirculation loop, the first recirculation pump and the second recirculation pump forming a single recirculation pump configured to recirculate digestate to the first injector and/or to the second injector.

Advantageously, the roof is made of metal.

Figures 3, 4:
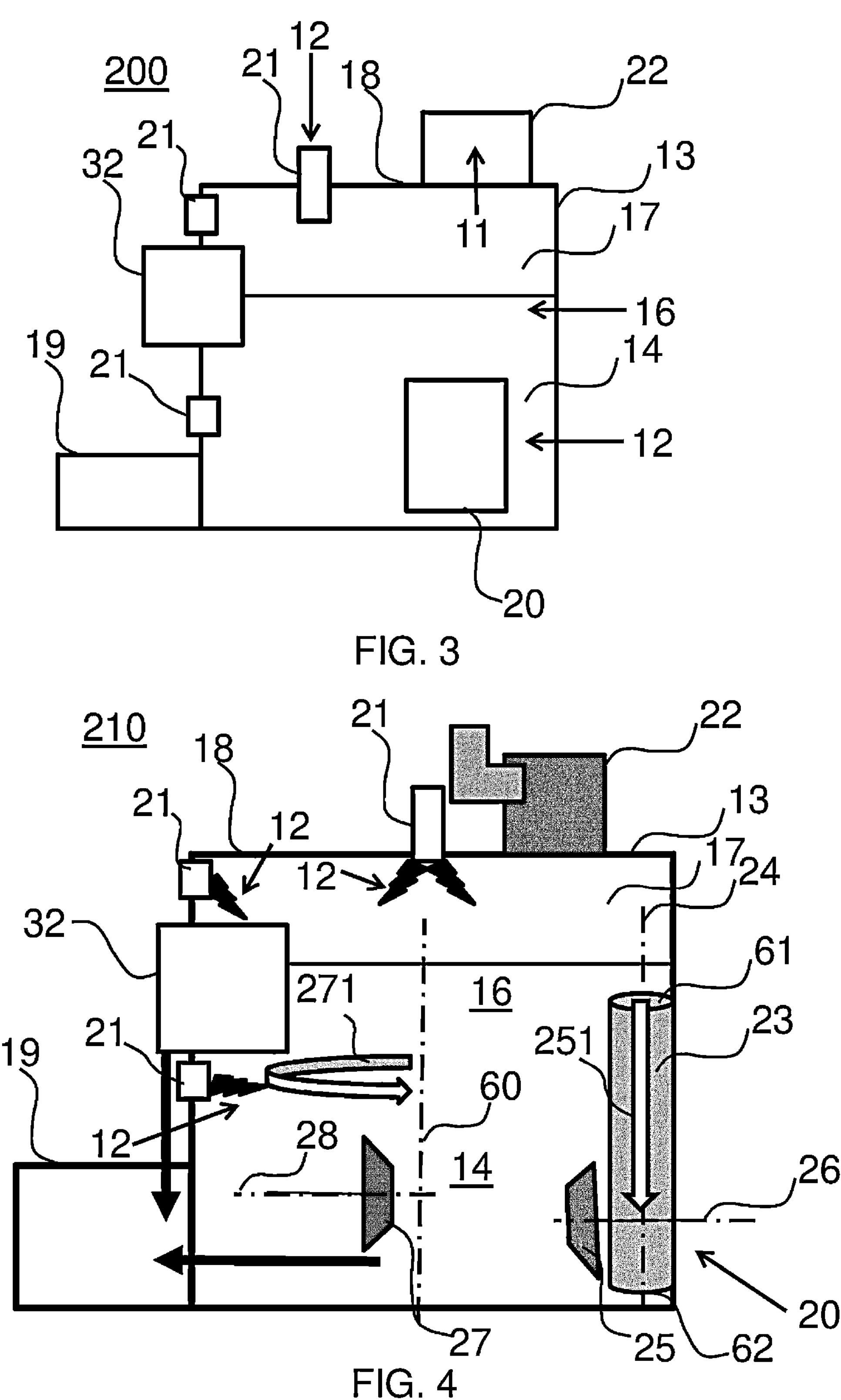
Figure 5:
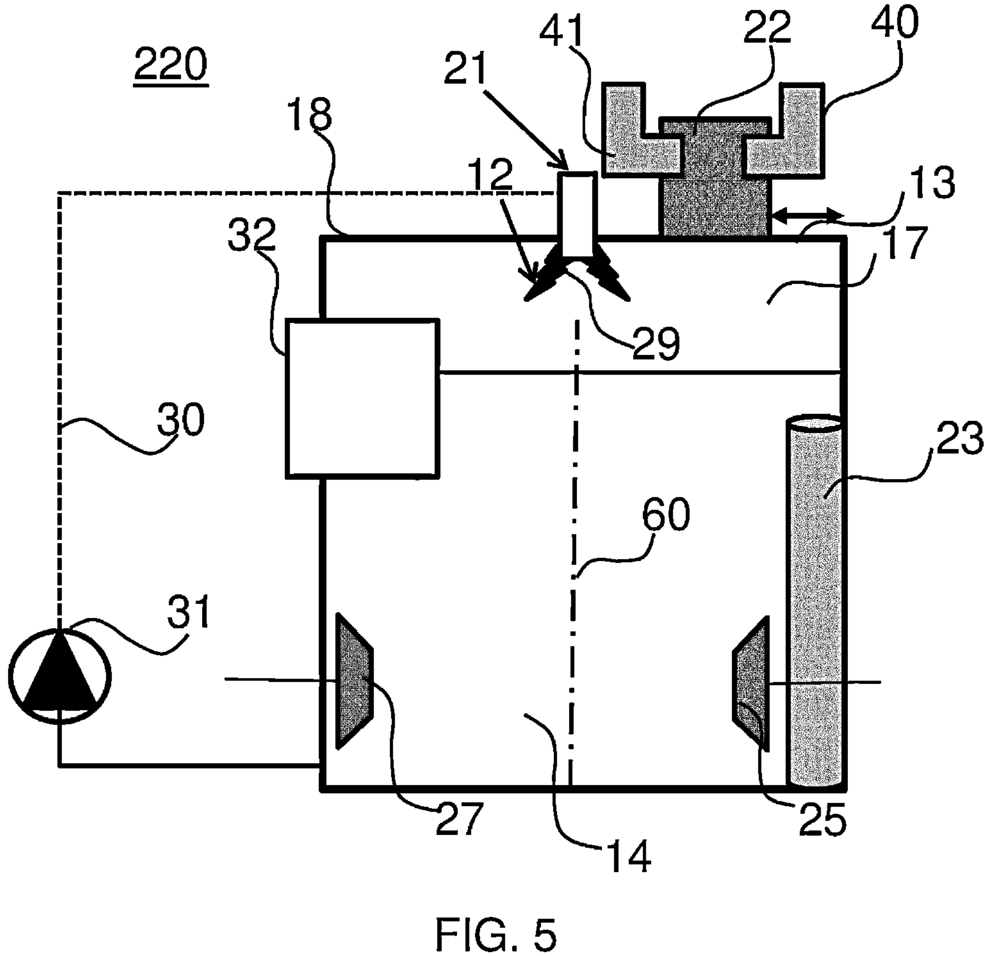
Figure 6:
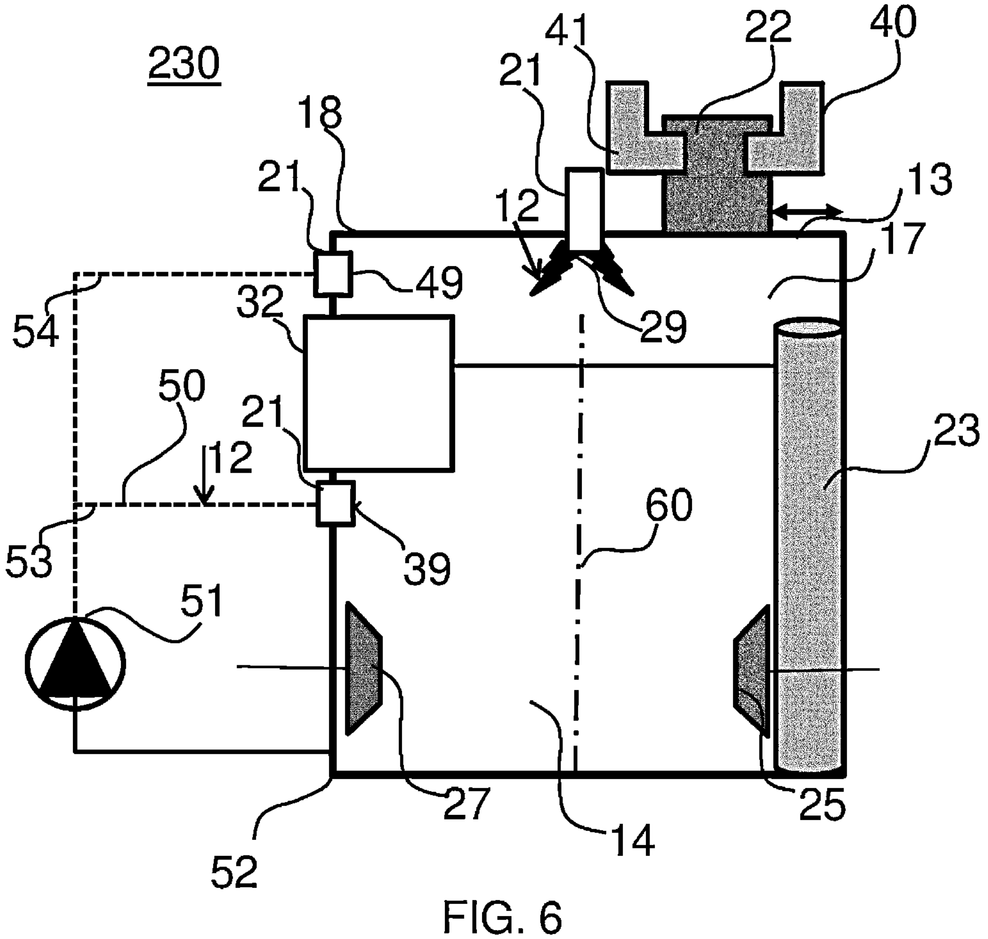
Figure 7:
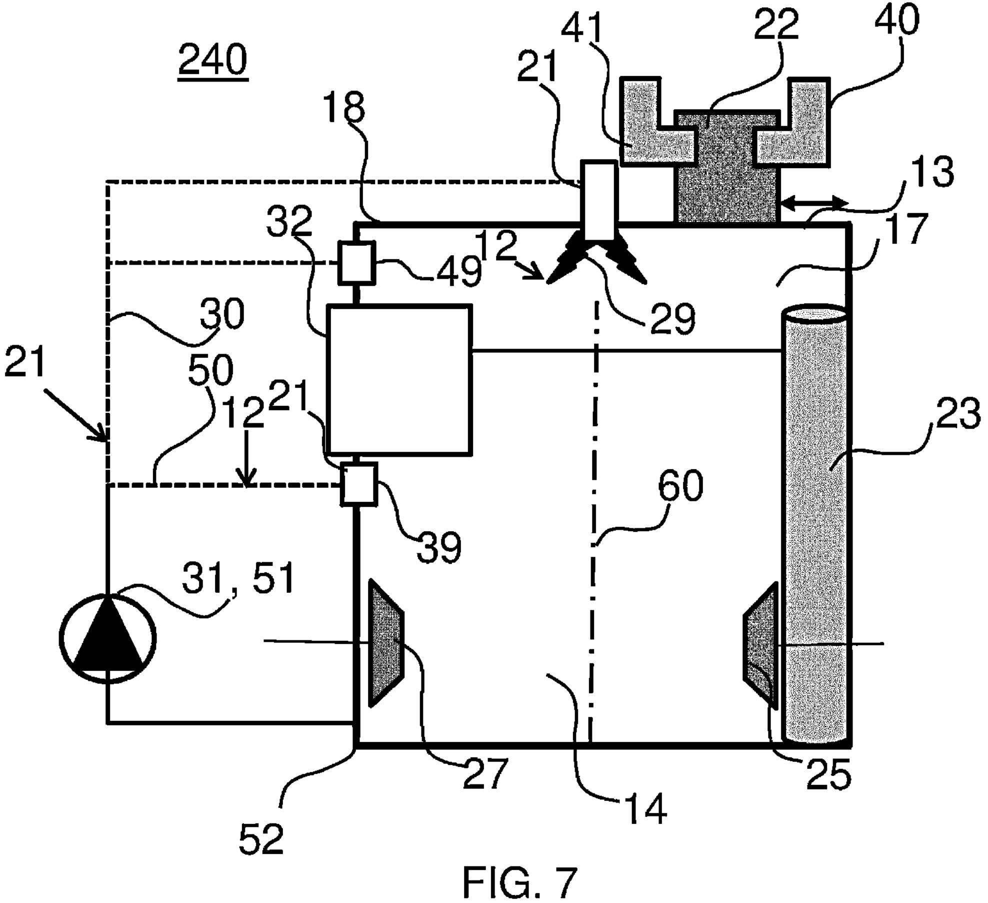
Figure 8:
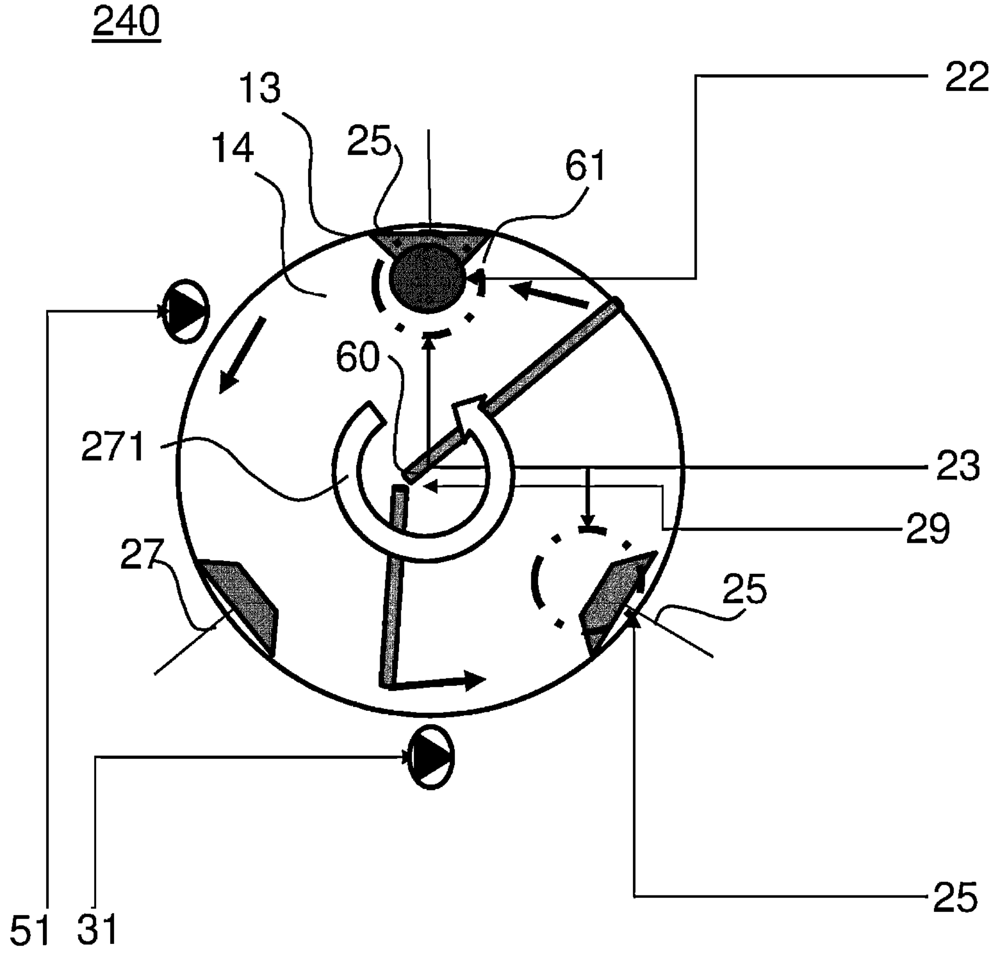

The invention will be better understood and other advantages will become apparent on reading the detailed description of an example embodiment, a description illustrated by the attached drawings in which:

FIG. 1 schematically shows a digester according to the invention;

FIG. 2 schematically shows a device for discharging the foaming and/or floating matter from a digester according to the invention;

FIG. 3 schematically shows an embodiment of a digester according to the invention;

FIG. 4 schematically shows another embodiment of a digester according to the invention;

FIG. 5 schematically shows another embodiment of a digester according to the invention;

FIG. 6 schematically shows another embodiment of a digester according to the invention;

FIG. 7 schematically shows another embodiment of a digester according to the invention;

FIG. 8 schematically shows a sectional view of an embodiment of the digester according to the invention.

These figures, for the sake of clarity are not to scale. Furthermore, the same elements will bear the same references across all the figures.

The invention generally applies to digesters of 50 to 16000 $m^3$, and advantageously from 500 to 7000 $m^3$.

FIG. 1 schematically shows a digester 10 according to the invention. The digester 10 is intended to perform a sludge methanization treatment to generate biogas 11 and a digestate 12. The digester 10 comprises an enclosure 13 intended to contain a volume of material 14, the volume of material 14 comprising the digestate 12. The enclosure 13 preferably has a circular cross-section. At its surface, the digestate comprises foaming and/or floating matter 16 coming from the sludge or being generated during the methanization treatment. The enclosure 13 defines a first volume 14 equal to the volume of material and a second volume 17 arranged above the first volume 14. The digester 10 comprises a roof 18 (or upper wall) intended to close the enclosure 13. It also comprises a reservoir 19 near the enclosure 13 and intended to collect the digestate 12. The reservoir 19 is connected to the enclosure. It may be contiguous with the enclosure or near the enclosure, so as to allow a gravity transfer of the digested sludge (the digestate 12) for example through a direct drop or an indirect drop by means of a slope. Finally, the digester 10 comprises a dome 22 arranged on a portion of the roof 18, and intended to collect the biogas 11.

According to the invention, the digester 10 comprises a device 32 for discharging the foaming and/or floating matter 16 of the digestate 12. The device 32 for discharging the foaming and/or floating matter 16 of the digestate 12 is shown schematically in FIG. 1. It is presented in detail below.

FIG. 2 schematically shows a device 32 for discharging foaming and/or floating matter 16 from a digester according to the invention. The device 32 for discharging foaming and/or floating matter 16 of the digestate 12 comprises a first tank 33 arranged in the enclosure 13 and delimited by a first wall 100, and a second tank 34 connected to the atmosphere and sited outside the enclosure 13. The discharge device 32 further comprises a conduit 37 connecting the first tank 33 to the second tank 34.

More precisely, the first tank 33 is intended to be fed with digestate 12 and with foaming and/or floating matter 16 from the volume of material 14 by overflow over the first wall 100.

The second tank 34 comprises a first zone 35 delimited by a second wall 103, and a second zone 36 in direct or indirect communication with the reservoir 19. The first zone 35 is intended to be fed with digestate 12 and with foaming and/or floating matter 16 from the first tank 33 through the conduit 37. The second zone 36 of the second tank 34 is intended to be fed with digestate from the first zone 35 of the second tank 34 by overflow over the second wall 103. The second zone 36 is connected to the reservoir 19. The second orifice 102 is positioned higher than or level with the first orifice 101. The term altitude is to be understood as a measurement of the height along an axis whereby the enclosure 13 extends.

The conduit 37 connects the first tank 33 via a first orifice 101 to the first zone 35 of the second tank 34 via a second orifice 102. In other words, the first orifice 101 is the interface between the first tank 33 and the conduit 37, and the second orifice 102 is the interface between the conduit 37 and the first zone 35 of the second tank 34. In order to facilitate the flow of the foaming and/or floating matter, the orifice 102 is located above or level with the orifice 101.

As can be seen in FIG. 2, the upper end of the first wall 100 is located at a first height h1 above a reference point 1001 of the first orifice 101. The upper end of the second wall 103 is located at a second height h2 above the reference point 1001 of the first orifice 101. The reference point 1001 of the first orifice 101 may be located at the lowest point of the first orifice 101. It may also be the center of the first orifice 101 (as shown in FIG. 2) in the case of an orifice with a circular cross-section. In other words, the two heights h1 and h2 are measured from the same altitude, that of the previously chosen reference point.

According to the invention, the first height h1 and the second height h2 are predefined such that a first mixture, containing variable proportions of digestate and foaming and/or floating matter in the first tank 33 and having a first average density d1, is transferred by gravity into the first zone 35, which contains a second mixture containing variable proportions of digestate 12 and foaming and/or floating matter 16 and having a second density d2, the transfer operating such that the product of the first average density d1 times the first height h1 is greater than the product of the second average density d2 times the second height h2) times the first height h1. In other words, the discharge of the foaming/floating matter 16 by the discharge device 32 takes place as long as the relationship d1*h1>d2*h2 is satisfied.

This relationship is established by omitting the head losses in the conduit 37 and the orifices 101, 102 as well as the difference between the pressure of the gas phase above the first tank 33 and the atmospheric pressure of the second tank 34. A more detailed calculation taking into account the impact of head losses and pressure differences can be achieved by a person skilled in the art who specializes in fluid mechanics. Such a calculation would only marginally modify the relationship stated above. In any case, when defining the first height h1 and the second height h2 such that a first medium density mixture d1 is transferred by gravity into the first zone 35 containing a second mixture of density d2 based on the relationship d1*h1>d2*h2, the transfer takes place. By taking into account the effects of head losses in the transfer pipe and its orifices (101, 37, 102) and of differential pressure between the digester and the outside, which a person skilled in the art knows how to determine, the transfer takes place for a mixture of density close to d1 or greater. Taking into account the effects of head losses and differential pressure of the digester will significantly impact the density of the mixture. More specifically, if h1 and h2 are defined from the relationship d1*h1>d2*h2, the device will allow the transfer of a mixture to a density very close to d1 (with a difference of the order of a few % relative to d1, a difference that a person skilled in the art knows how to determine with consideration of all the effects mentioned).

By way of illustration and in a non-limiting manner, the discharge device 32 can be sized based on extreme assumptions that are unfavorable to the flow from the tank 33 to the tank 34. Thus and by way of example, the maximum density value d2 can be considered equal to 1.05 and corresponding to a dense digestate that does not contain foaming and/or floating matter. Likewise, the minimum density value d1 can be considered to be equal to 0.3 and to correspond to a mixture consisting essentially of foaming and/or floating matter. Based on the above relationship, it is deduced therefrom that when h1>3.5×h2 (with 3.5=1.05/0.3), then a mixture of density 0.3 or more may be discharged by gravity flow from the tank 33 to the tank 34 containing a mixture of density 1.05 or less. The values of the heights h1, h2 are generally set when the digester is constructed with the discharge device 32. However, it is also possible to provide walls 100 and/or 103 with variable heights h1 and h2, which can be adjusted subsequently to the manufacture and/or installation of the discharge device 32.

By virtue of the device 32 for discharging foaming/floating matter 16, the discharge of the foaming/floating matter can be carried out by overflow concurrent with a regular and continuous operation of the digester.

FIG. 3 schematically shows an embodiment of a digester 200 according to the invention; The digester 200 shown in FIG. 3 is identical to the digester 10 shown in FIG. 1. The digester 200 further comprises a device 20 for mixing the volume of material 14 disposed in the first volume 14. The mixing device 20 is configured to move the volume of material 14. The mixing device 20 imparts a rotational movement to the volume of material 14 in such a way that the foaming and/or floating matter 16 driven with the digestate 12 are extracted from the volume of material 14 along with the digestate 12 by overflow 100 into the first tank 33. The mixing device 20 makes it possible to avoid the accumulation of foaming and/or floating matter 16 at a point on the surface of the volume of material 14 away from the first tank 33.

The digester 200 may further comprise a device 21 for injecting digestate 12 into the second volume 17 and/or into the volume of material 14. The injection device 21 makes it possible to inject digestate 12 into the second volume 17 above the volume of material 14. The injection device 21 is preferably arranged at the center of the roof 18. The injection of digestate 12 above the volume of material 14 serves to project the foaming and/or floating matter 16, which tends to accumulate at the center of the surface, toward the periphery where it is driven toward the first tank 33 to be extracted from the volume of material 14. The foaming and/or floating matter 16 is driven toward the tank 33 by the rotational movement of the volume of material 14 generated by the mixing device 20.

The injection device 21 can also be located at the periphery of the enclosure 13. The injection of digestate 12 from the lateral wall above the volume of material 14 is carried out with a jet oriented so as to produce a rotational movement of the volume of material around a vertical axis. This rotational movement drives the foaming and/or floating matter towards the tank 33.

FIG. 4 schematically shows another embodiment of a digester 210 according to the invention; In this embodiment, the digester 210 comprises the injection device 21 and the mixing device 20. Although the presence of these two devices is preferred, the invention also covers any digester that comprises only an injection device 21 or only a mixing device 20.

The mixing device 20 comprises one or more chimneys 23 extending into the enclosure 13 along a first axis 24, preferably at the periphery of the enclosure 13. Each chimney 23 has an upper end 61 and a lower end 62. The term "chimney" is understood to mean a hollow body extending along the first axis 24. The chimneys 23 may have a circular or polygonal cross-section. In a preferred embodiment, the chimneys are half-cylinders fixed, for example by welding or riveting, to the side wall of the enclosure 13. The mixing device 20 comprises one or more first mixers 25. Each of the first mixers 25 is associated with one of the plurality of chimneys 23. In other words, each chimney 23 has its own first mixer 25. Each of the first mixers is preferably positioned under the lower end 62 of its chimney 23. The first mixer(s) 25 are configured to move the volume of material 14 in rotation around a vertical central axis 60, substantially parallel to the first axis 24, and in translation along the first axis 24 from the upper end 61 toward the lower end 62 of said chimney 23. In other words, the first mixers 25 are oriented so as to impart a rotational movement to the digestate 12 according to the movement represented by the arrow 271 and an upward movement in the volume 14 via the opposite downward movement through the chimney 23 shown by the arrow 251. We can term this movement a combination of a horizontal rotation about the axis 60 and vertical movement from the top of the chimney to the bottom of the enclosure. The flow of digestate through the suction of the mixer 25 is channeled from the surface by means of the chimney 23. This creates the vertical movement, and the orientation of the mixer 25 creates a horizontal rotation in addition to the rotation generated by the lateral injection device 21. The upper end 61 of the chimney(s) 23 is positioned under the surface of the material of the volume of material 14 (for example 250 mm under the lowest level of digestate). Thus, the digestate 12 falls into the chimney(s) 23. The assembly formed by a chimney 23 and a first mixer 25 contributes to de-laminating the volume of material 14 by producing an upward pumping of the volume of material 14.

Preferably, fresh sludge can be injected into the chimney 23 to promote an effective mixing of the fresh sludge with the remainder of the digestate. By way of example, the fresh sludge feed flow rate can be of the order of 30 m3/h whereas the pumping flow rate provided by a first mixer 25 can be of the order of 2500 m3/h, i.e. a ratio of the order of 1/100.

The mixing device 20 may also comprise one or more second mixers 27, each being arranged in the enclosure 13, preferably in the bottom of the enclosure 13, and more preferably at the periphery of the enclosure 13. The second mixers 27 are configured to move the volume of material 14 in rotation around the vertical central axis 60, substantially parallel to the first axis 24. Thus, the second mixers 27 are oriented so as to impart a rotational movement to the digestate 12 according to the movement represented by the arrow 271. We can term this movement a horizontal rotational movement. A person skilled in the art knows how to determine the appropriate characteristics (size, shape, rotation speed, etc.) of the mixers 25, 27 and orient the axes 26, 28 of the mixers 25, 27 as a function of the viscosity of the material to be stirred and the volume of material 14 considered.

The horizontal movement displaces the foaming/floating matter towards the periphery of the enclosure. The vertical movement displaces the foaming/floating matter from the upper surface of the volume of material 14 toward the bottom of the enclosure. The combination of these two movements makes it possible to prevent the formation and/or stagnation of foaming/floating matter on the surface of the volume of material and a better mixing of the contents of the enclosure is achieved.

FIG. 5 schematically shows another embodiment of a digester 220 according to the invention. In this embodiment, the digestate injection device 21 comprises a first injector 29 attached to the roof, preferably to the center of the roof, and in fluid connection with the second volume 17 and configured to inject the digestate 12 into the second volume 17. The injection device 21 comprises a first recirculation loop 30 between the first volume 14 and the first injector 29. Finally, the injection device 21 comprises a first recirculation pump 31 configured to recirculate the digestate 12 in the first recirculation loop 30 from the first volume 14 to the first injector 29. The injection of digestate into the second volume is meant to break up the foaming/floating matter and to make it move toward the periphery of the enclosure.

The dome 22 may comprise two safety valves 40, 41 arranged opposite each other.

The roof 18 is generally substantially flat. If it is made of metal, it may be either concave (if the pressure applied to the roof is less than 5 mbar), or convex (if the pressure applied to the roof is greater than 5 mbar).

FIG. 6 schematically shows another embodiment of a digester 230 according to the invention. In this embodiment, the digestate injection device 21 comprises a second injector 39 attached to a side wall of the enclosure 13 at a first height 53 and in fluid connection with the enclosure 13, and more precisely the volume of material 14, and configured to inject the digestate 12 into the enclosure 13, into the volume of material 14. The injection device 21 comprises a second recirculation loop 50 between a second height 52 of the enclosure 13, less than the first height 53 and the second injector 39. Finally, the injection device 21 comprises a second recirculation pump 51 configured to recirculate the digestate 12 in the second recirculation loop 30 from the second height 52 of the enclosure 13 and to the second injector 39. In other words, the injection device of the digester 130 is configured to inject the digestate initially into the lower part of the enclosure to a high part of the volume of material. As already mentioned, this injection contributes to placing the material of the enclosure in motion and to rotate the foaming/floating matter on the surface to prevent their stagnation and send them towards the periphery of the enclosure, toward the chimneys 23 and the tank 33. Alternatively, or additionally, the digestate injection device 21 comprises a second injector 49 attached to a side wall of the enclosure 13 at a first height 54 and in fluid connection with the enclosure 13 and configured to inject the digestate 12 into the enclosure 13 at the first height 54, the first height 54 being at the level of the second volume 17. In a similar manner to what was explained above, the injection device 21 comprises a second recirculation loop 50 between a second height 52 of the enclosure 13, less than the first height 54 and the second injector 49. Additionally, the injection device 21 comprises a second recirculation pump 51 configured to recirculate the digestate 12 in the second recirculation loop 30 from the second height 52 of the enclosure 13 and to the second injector 49. This injection of digestate 12 above the volume of material 14 forms a jet oriented relative to the upper surface of the volume of material 14 so as to produce a rotational movement of the volume of material around the vertical axis 60. This rotational movement drives the foaming and/or floating matter towards the tank 33.

This embodiment may comprise a single second injector 39, 49 on the side wall of the enclosure. However, it may also comprise a plurality of second injectors 39, 49 distributed all around the wall, with one or more recirculation loops adapted to this configuration, in connection with the second recirculation pump.

The digester according to the invention may comprise either one of the two recirculation loops, or a double recirculation, that is, both of the recirculations described above, with the first recirculation loop and the second recirculation loop. In a preferred embodiment, the two recirculation loops are combined.

FIG. 7 schematically shows another embodiment of a digester 240 according to the invention. In this embodiment of the digestion according to the invention, the first recirculation loop 30 and the second recirculation loop 50 are grouped into one and the same recirculation loop, the first recirculation pump 31 and the second recirculation pump 51 forming a single recirculation pump configured to recirculate digestate 12 to the first injector 29 and/or to the second injector 39, in alternating or simultaneous fashion. Alternatively, or additionally, the second recirculation loop can be connected to the second injector 49 attached to the side wall of the enclosure 13 at the first height 54 and in fluid connection with the enclosure 13 and configured to inject the digestate 12 into the enclosure 13 at the first height 54, into the volume 17.

FIG. 8 schematically shows a sectional view of an embodiment of the digester 240 according to the invention. The cut is made at the enclosure 13, perpendicular to the central vertical axis 60, revealing the elements present in (or connected to) the enclosure 13 in order to better represent the digester of the invention. It should be noted that the device for discharging the foam/floating matter is not shown in this figure.

At the periphery of the enclosure 13, that is, near the side walls of the enclosure, a second mixer 27 is present to impart a so-called horizontal rotational movement (shown by the arrow 271) to the volume of material 14 and therefore to the foaming/floating matter located on the upper surface of the volume of material. A single second mixer 27 is shown but there could be more than one. The mixer(s) 27 can be located at the periphery of the enclosure 13 but can also be located closer to the center of the enclosure. Two first mixers 25 are present to impart a so-called vertical rotational movement to the volume of material 14 and therefore to the foaming/floating matter located on the upper surface of the volume of material. The first mixers 25 are each positioned under a chimney 23. Thus, the foaming/floating matter present on the surface of the volume of material 14 is moved from the center toward the periphery by the horizontal rotational movement owing to the second mixers 27. Next, having arrived at the periphery of the enclosure 13, the foaming/floating matter goes down through the chimneys 23 following the vertical rotational movement generated by the first mixers 25. The injection of additional sludge into the chimneys 23 contributes to an effective mixing of the sludge injected with the remainder of the digestate already present in the enclosure.

Two recirculation pumps 31, 51 are shown. The first recirculation pump 31 is associated with the first recirculation loop (not shown) and aims to inject the digestate 12 taken from the bottom of the enclosure 13 into the headspace (second volume 17) by the first injector 29. The digestate is injected by the first injector above the volume of material 14, on the foaming/floating matter present on the surface. The foaming/floating matter is thus broken up. This injection also contributes to causing them to move towards the periphery of the enclosure.

The second recirculation pump 51 is associated with the second recirculation loop (not shown) and aims to inject the digestate 12 taken from the bottom of the enclosure 13 into the volume of material 14 at a height greater than the height from which the digestate was taken. This lateral injection moves the volume of material and helps to move the foaming/floating matter on the surface by initiating a rotational movement to prevent their stagnation and send them towards the periphery of the enclosure, toward the chimneys 23. In other words, the second recirculation loop aims to inject digestate from a lower level of the enclosure into the digestate at a higher level of the enclosure in order to decompress the volume of material. The second recirculation pump 51 associated with the second recirculation loop (not shown) can also aim to inject the digestate 12 taken from the bottom of the enclosure 13 into the volume of material 14 at a height above where the digestate was taken from, in order to inject the collected digestate into the second volume, above the volume of material 14. This injection contributes to the rotational movement of the volume of material around the vertical axis 60. This rotational movement drives the foaming and/or floating matter towards the tank 33.

As explained above, the first recirculation loop 30 and the second recirculation loop 50 can be grouped into a single recirculation loop. This single recirculation loop can be supplied by the first recirculation pump 31 and the second recirculation pump 51. Alternatively, the first recirculation pump 31 and the second recirculation pump 51 can form a single recirculation pump configured to recirculate the digestate 12 toward the first injector 29 and toward the second injector 39, 49, in either simultaneous or alternating fashion.

Finally, the digester 240 further comprises a dome 22 arranged on a portion of the roof 18, and intended to collect the biogas 11. Advantageously, the dome is arranged substantially above a chimney 23. The mixture of digestate 12, foaming/floating matter 16 and freshly introduced sludge, which takes place in the chimney 23, can make it possible to release pockets of biogas which will escape through the upper end 61 of the chimney 23. It is therefore judicious to position the dome 22 near the upper end 61 of the chimney 23.

Advantageously, the dome is arranged substantially at the periphery of the roof 18 and above a second injector 39 attached to the side wall of the digester in the volume 17. The injection of digestate 12 by the injector causes a mechanical foam-breaking effect that therefore protects the dome from any intrusion of foam.

In one particular embodiment of the invention, the digester may further comprise a valve arranged downstream of the second tank 34, for example on a conduit at the outlet of the second tank 34. It may be any type of suitable valve, such as a sleeve valve (pneumatic or mechanical) or a guillotine valve. The valve makes it possible to control the discharge rate of the contents of the second tank 34. When the valve is in the closed position, there is no discharge of the contents toward the reservoir 19. This makes it possible to increase the level of the content in the enclosure of the digester by a few centimeters and thus facilitate the driving-out of the foaming/floating matter by an instantaneous opening of the valve. Such an opening of the valve causes a discharge by flushing. The digester may optionally comprise a device for activating the valve to open it and close it. The digester may also comprise a timer intended to trigger the valve activation device at predefined time intervals, so as to allow preventive discharge of the foaming and floating matter. This results in better control of the amount of foaming/floating matter in the enclosure of the digester.

The invention proposes a reduced-headspace digester that makes it possible to discharge foaming/floating matter regardless of its density and to maintain the integrity of the structure in case of an RVE phenomenon. This is made possible by the device for discharging the foaming/floating matter, operating by gravity with a double overflow device. In addition, the injection device makes it possible to move the foaming/floating matter toward the periphery of the enclosure, and the mixing device also contributes to moving the foaming/floating matter towards the bottom of the enclosure. The combination of the injection device and the mixing device ensures both a very good stirring of the foaming and/or floating matter with the digestate in order to promote their reincorporation into the digestate, along with good discharging of the non-reincorporated foaming and/or floating matter by overflow.

The invention also relates to a digestion method for performing a sludge methanization treatment to generate biogas 11 and a digestate 12 in a digester as described above. At its surface, the digestate comprises foaming and/or floating matter 16 coming from the sludge or generated during the methanization treatment. The digestion method according to the invention comprises a step of managing the foaming and/or floating matter by discharging according to its density. This management step comprises:

- a step of feeding the first tank 33 with digestate 12 and with foaming and/or floating matter 16 from the volume of material 14 by overflow over the first wall 100, and
- a step of feeding the first zone 35 of the second tank 34 with digestate 12 and with foaming and/or floating matter 16 from the first tank 33 via the conduit 37,
- a step of feeding the second zone 36 of the second tank 34 with digestate from the first zone 35 of the second tank 34 by overflow over the second wall 103.

As described above, the conduit 37 connects the first tank 33 via the first orifice 101 to the first zone 35 of the second tank 34 via a second orifice 102, the second orifice 102 being situated higher than or level with the first orifice 101, and the upper end of the first wall 100 being situated at a first height h1 above a reference point of the first orifice 101 and the upper end of the second wall 103 being situated at a second height h2 above the reference point of the first orifice 101. The first height h1 and the second height h2 are predefined such that a first mixture, containing variable proportions of digestate and foaming and/or floating matter in the first tank 33 and having a first average density d1, is transferred by gravity into the first zone 35, which contains a second mixture containing variable proportions of digestate and foaming and/or floating matter and having a second density d2, the transfer operating such that the product of the first average density d1 times the first height h1 is greater than the product of the second average density d2 times the second height h2) times the first height h1.

Advantageously, the digestion method according to the invention further comprises a step of mixing the volume of material 14.

Advantageously, the digestion method according to the invention further comprises a step of injecting digestate into the volume of material 14 and/or into the volume 17.

It will appear more generally to a person skilled in the art that various modifications can be made to the embodiments described above, in light of the teaching disclosed herein. In the following claims, the terms used should not be interpreted as limiting the claims to the embodiments disclosed in the present description, but must be interpreted to include therein all equivalents that the claims aim to cover due to their wording and which may be foreseen within the reach of a person skilled in the art based on their general knowledge.

The invention claimed is:

1. A digester adapted to perform a sludge methanization treatment for generating biogas and a digestate, the digester comprising:

an enclosure adapted to contain a volume of material, the volume of material comprising the digestate, the digestate comprising, at a surface, at least foaming or floating matter coming from sludge or generated during the methanization treatment, the enclosure defining a first volume equal to the volume of material and a second volume arranged above the first volume;

a roof adapted to close the enclosure;

a reservoir near the enclosure and adapted to collect the digestate;

a dome arranged on a portion of the roof and adapted to collect the biogas;

a device for discharging the at least foaming or floating matter comprising:

a first tank arranged in the enclosure, the first tank being submerged in the volume of material and delimited by a first wall, the first tank being adapted to be fed with the digestate and with the at least foaming or floating matter from the volume of material by overflow over the first wall;

a second tank connected to the atmosphere and sited outside the enclosure, comprising:

a first zone delimited by a second wall; and a second zone in communication with the reservoir;

a conduit that connects the first tank via a first orifice to the first zone of the second tank via a second orifice, wherein the first zone is adapted to be fed with the digestate and with the at least foaming or floating matter from the first tank through the conduit, the second zone of the second tank is adapted to be fed with digestate from the first zone of the second tank by overflow over the second wall, the second orifice is positioned higher than or level with the first orifice, an upper end of the first wall is located at a first height above a reference point of the first orifice and an upper end of the second wall is located at a second height above the reference point of the first orifice and the upper end of the second wall is positioned lower than the upper end of the first wall, the first height and the second height are predefined based on a ratio between a first average density of a first mixture, containing variable proportions of the digestate and the at least foaming and/or floating matter in the first tank that is transferred by gravity into the first zone and a second average density of a second mixture containing variable proportions of the digestate and the at least foaming or floating matter in the first zone.

2. The digester according to claim 1, further comprising a device for mixing the volume of material disposed in the first volume, the mixing device being configured to move the volume of material.

3. The digester according to claim 2, wherein the mixing device comprises:

one or more chimneys extending into the enclosure along a first axis, each chimney having an upper end and a lower end;

one or more first mixers, the one or more first mixers(s) being configured to move the volume of material in rotation around a vertical central axis, substantially parallel to the first axis, and in translation along the first axis from the upper end toward the lower end of said one or more chimneys.

4. The digester according to claim 2, wherein the mixing device comprises one or more second mixers, each being arranged in the enclosure, the second mixers being configured to move the volume of material in rotation around a vertical central axis, substantially parallel to the first axis.

5. The digester according to claim 1, further comprising a device arranged in the volume of material for injecting the digestate into the second volume.

6. The digester according to claim 5, wherein the digestate injection device comprises:

a first injector attached to the roof and in fluid connection with the second volume and configured to inject digestate into the second volume;

a first recirculation loop between the first volume and the first injector;

a first recirculation pump configured to recirculate the digestate in the first recirculation loop from the first volume to the first injector.

7. The digester according to claim 5, wherein the digestate injection device further comprises:

a second injector attached to a side wall of the enclosure at a first height and in fluid connection with the enclosure and configured to inject digestate into the enclosure at the first height;

a second recirculation loop between a second height of the enclosure, which is less than the first height, and the second injector;

a second recirculation pump configured to recirculate the digestate in the second recirculation loop from the second height of the enclosure and to the second injector.

8. The digester according to claim 7, wherein the first recirculation loop (30) and the second recirculation loop are grouped into one and the same recirculation loop, the first recirculation pump and the second recirculation pump forming a single recirculation pump configured to recirculate digestate to the first injector and/or to the second injector.

9. The digester according to claim 1, wherein the roof is made of metal.

10. The digester according to claim 1, where a first product of the first average density times the first height is greater than a second product of the second average density times the second height.

11. The digester according to claim 1, wherein the second average density is greater than the first average density.

* * * * *